US010161012B2

(12) United States Patent
Wang et al.

(10) Patent No.: US 10,161,012 B2
(45) Date of Patent: Dec. 25, 2018

(54) METHOD AND KIT FOR THE FIELD DIAGNOSIS OF CAPRINE ARTHRITIS-ENCEPHALITIS VIRUS (CAEV) INFECTION

(71) Applicant: National Taiwan University, Taipei (TW)

(72) Inventors: Pei-Hwa Wang, Taipei (TW); Po-An Tu, Taipei (TW); Fang-Yu Lai, Taipei (TW); Jen-Wen Shiau, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 58 days.

(21) Appl. No.: 15/439,359

(22) Filed: Feb. 22, 2017

(65) Prior Publication Data

US 2018/0237868 A1   Aug. 23, 2018

(51) Int. Cl.
```
C12Q 1/70      (2006.01)
C12Q 1/682     (2018.01)
C12Q 1/6858    (2018.01)
C12Q 1/6853    (2018.01)
G01N 33/558    (2006.01)
G01N 33/543    (2006.01)
```
(52) U.S. Cl.
CPC ............ *C12Q 1/702* (2013.01); *C12Q 1/682* (2013.01); *C12Q 1/6853* (2013.01); *C12Q 1/6858* (2013.01); *G01N 33/54313* (2013.01); *G01N 33/558* (2013.01)

(58) Field of Classification Search
None
See application file for complete search history.

(56) References Cited

U.S. PATENT DOCUMENTS

2015/0240298 A1*  8/2015  Piepenburg ............... 435/6.11

OTHER PUBLICATIONS

GenBank: M33677.1, Caprine arthritis encephalitis virus, complete proviral genome (Year: 1996).*
Po-An Tu et al; "Development of a recombinase polymerase amplification lateral flow dipstick (RPA-LFD) for the field diagnosis of caprine arthritis-encephalitis virus ( CAEV) infection" Journal of Virological Methods 243 (2017), p. 98-104.

* cited by examiner

*Primary Examiner* — Michelle S Horning
(74) *Attorney, Agent, or Firm* — Muncy, Geissler, Olds & Lowe, P.C.

(57) ABSTRACT

The invention is to provide a method and kit based on recombinase polymerase amplification (RPA) and lateral flow dipstick (LFD) for detection of caprine arthritis-encephalitis virus (CAEV) infection. The method and kit are suitable for both laboratory and field application, and are specific and sensitive for detecting CAEV proviral DNA in goats in a fast manner. The method and lit of the invention are also applicable for on-site utilization at farms and should be useful in both eradication programs and epidemiological studies.

13 Claims, 4 Drawing Sheets
Specification includes a Sequence Listing.

SEQUENCE LISTING

<160> NUMBER OF SEQ ID NOS: 4

<210> SEQ ID NO 1
<211> LENGTH: 32
<212> TYPE: DNA
<213> ORGANISM: Unknown
<220> FEATURE:
<223> OTHER INFORMATION: forward primer
<220> FEATURE:
<221> NAME/KEY: primer_bind
<222> LOCATION: (1)..(32)

<400> SEQUENCE: 1
tcagagggga gcacttgaca gaaggaaatt gt                          32

<210> SEQ ID NO 2
<211> LENGTH: 29
<212> TYPE: DNA
<213> ORGANISM: Unknown
<220> FEATURE:
<223> OTHER INFORMATION: reverse primer
<220> FEATURE:
<221> NAME/KEY: primer_bind
<222> LOCATION: (1)..(29)

<400> SEQUENCE: 2
ctaatgtggc ctgcaaagac ataaagtct                              29

<210> SEQ ID NO 3
<211> LENGTH: 30
<212> TYPE: DNA
<213> ORGANISM: Unknown

```
<220> FEATURE:
<223> OTHER INFORMATION: probe
<220> FEATURE:
<221> NAME/KEY: misc_feature
<222> LOCATION: (1)..(30)

<400> SEQUENCE: 3
ggggagcact tgacagaagg aaattgttta                                          30

<210> SEQ ID NO 4
<211> LENGTH: 15
<212> TYPE: DNA
<213> ORGANISM: Unknown
<220> FEATURE:
<223> OTHER INFORMATION: downstream of the probe
<220> FEATURE:
<221> NAME/KEY: misc_feature
<222> LOCATION: (1)..(15)

<400> SEQUENCE: 4
ggtgccttaa aacat                                                          15
```

METHOD AND KIT FOR THE FIELD DIAGNOSIS OF CAPRINE ARTHRITIS-ENCEPHALITIS VIRUS (CAEV) INFECTION

BACKGROUND OF THE INVENTION

1. Field of the Invention

The present invention relates to method and kits for use in detecting caprine arthritis-encephalitis virus (CAEV) infection, more specifically, the present invention relates to method and kit using recombinase polymerase amplification lateral flow dipstick (RPA-LFD) for the field diagnosis of CAEV detection.

2. Description of the Related Art

Caprine arthritis-encephalitis virus (CAEV) is one of the small ruminant lentiviruses (SRLVs), and belongs to the genus *Lentivirus* and the family Retroviridae. The virus can infect goats and occasionally sheep and other related ruminants. Epidemiological evidence indicates that the major transmission route of this virus is through the ingestion of colostrum from CAEV-infected adult goats by lambs and iatrogenic transmission or lateral transmission through long-term close contact with infected goats. All breeds and ages are susceptible to the virus and, once an animal is infected, the virus persists throughout the carrier's lifetime. Although most infected goats remain asymptomatic, all carriers continuously shed the virus to the environment, leading to more infections among naive goats.

There is no effective medication for the treatments of CAEV infections, nor is there any vaccine that can prevent such infections. As such, accurate diagnosis followed by the immediate culling of CAEV-positive animals from the herd is the major practice for reducing potential economic losses due to the disease. The tests most commonly used to diagnose CAE are the serological tests recommended by the World Animal Health Organization, such as the agar gel immunodiffusion (AGID) test which is based on CAEV serology. However, the AGID method tends to underestimate the infection incidence when infected animals exhibit delayed sera conversion. This delayed sera conversion impedes the early and precise serological diagnosis and presents a possible infection hot source. In Taiwan, the routine laboratory diagnosis of CAEV infection is based on the enzyme-linked immunosorbent assay (ELISA). In this assay, recombinant capsid (CA) proteins or the transmembrane (TM) domains of envelope glycoprotein subunits are used as antigens, and the assay has proven to be more sensitive than AGID. However, the antigenic heterogeneity of CA proteins and TM domains may result in a loss of sensitivity if the animal being tested was infected with a CAEV strain different from that employed in the ELISA. Moreover, the preparation of antigen is expensive and time-consuming, making the assay impractical for field diagnosis.

Therefore, there remains a need for a lower cost, easier implement, more comprehensive and rapid approach with high sensitivity and specificity.

SUMMARY OF THE INVENTION

One aspect of the invention is to provide a method for detection of caprine arthritis-encephalitis virus (CAEV) infection, comprising the steps of: (a) amplifying gag-segment (nt 618-803) DNA of CAEV as a target sequence in the sample by recombinase polymerase amplification (RPA) in the presence of a pair forward and reverse primers and a probe sequence which is complementary to an internal region of the target sequence, wherein one of the primers being labeled with a first label and the probe sequence being labeled with a second label such that amplification of the target sequence generates an amplicon labeled with both first and second labels; (b) applying an amount of the amplification product of step (a) to a lateral flow device/strip to flow laterally towards a distal end of the lateral flow device/strip, wherein the lateral flow device/strip sequentially comprising (i) a sample pad, (ii) a conjugate pad, (iii) a test region, and (iv) a control region, said conjugate pad having mobile reporter labeled with a first agent which specifically binds to the first label or the second label of the amplicon, said test region provided with a second agent which specifically binds to the second label or the first label of the amplicon to inhibit further lateral flow of the amplicon associated with the mobile reporter, and said control region being provided with a control agent; and (c) detecting any binding of the amplification product at the test region and the control region.

Another aspect of the present invention is to provide a kit for detection of caprine arthritis-encephalitis virus (CAEV) in a sample, comprising: a pair of forward and reverse primers targeting a gag-segment (nt 618-803) DNA of CAEV as a target sequence; a probe sequence which is complementary to an internal region of the target sequence; a reagent for conducting recombinase polymerase amplification (RPA) reaction; and a lateral flow device/strip; wherein one of the primers being labeled with a first label and the probe sequence being labeled with a second label such that amplification of the target sequence generates an amplicon labeled with both first and second labels; and the lateral flow device/strip sequentially comprising (i) a sample pad, (ii) a conjugate pad, (iii) a test region, and (iv) a control region, said conjugate pad having mobile reporter labeled with a first agent which specifically binds to the first label or the second label of the amplicon, said test region provided with a second agent which specifically binds to the second label or the first label and said control region being provided with a control agent.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore, not to be intended to limit its scope, the disclosure will be described with specificity and detail through use of the accompanying drawings, in which:

FIGS. 2(A)-2(B) show molecular specificity of RPA-AGE (agarose gel electrophoresis) and RPA-LFD carried out using total DNA of animal natural infected with goat pox virus (GPV) and bovine leukaemia virus (BLV) as template.

FIGS. 3(A)-3(B) show molecular sensitivity test results of RPA using 5-fold serially diluted total DNA extracted from CAEV-infected goat as template.

FIGS. 4(A)-4(B) show molecular sensitivity test of RPA using 10-fold serially diluted plasmid DNA as templates.

DETAILED DESCRIPTION OF THE PREFERRED EMBODIMENTS

Hereinafter, illustrative embodiments and examples of the present disclosure will be described in detail with reference to the accompanying drawings so that inventive concept may be readily implemented by those skilled in the art.

Throughout the whole document, the term "comprises or includes" and/or "comprising or including" used in the document means that one or more other components, steps, operations, and/or the existence or addition of elements are not excluded in addition to the described components, steps, operations and/or elements. The terms "about or approximately" or "substantially" are intended to have meanings close to numerical values or ranges specified with an allowable error and intended to prevent accurate or absolute numerical values disclosed for understanding of the present invention from being illegally or unfairly used by any unconscionable third party. The terms "a" and "an" refer to one or to more than one (i.e., to at least one) of the grammatical object of the article.

The method described in this disclosure can detect DNA sequences (such as pathogen DNA) without the use of optical fluorescence techniques. The present method uses RPA assay and lateral flow detection to amplify and detect, respectively, specific DNA sequences in a variety of sample types. The RPA assay is isothermal and employs phage-derived recombinase UvsX which, assisted by its cofactor UvsY, aggregates with two oligonucleotide primers to scan for a homologous target sequence in a DNA template. Upon identifying the specific homologous sequence, strand invasion and consequent strand displacement amplification occur via the *Staphylococcus aureus*-derived DNA polymerase (Sau DNA polymerase) to generate double-stranded DNA (dsDNA) in a similar manner to PCR.

[Method of the Invention]

The method of the invention, in a first aspect, for detection of caprine arthritis-encephalitis virus (CAEV) infection, comprising the steps of: (a) amplifying gag-segment (nt 618-803) DNA of CAEV as a target sequence in the sample by recombinase polymerase amplification (RPA) in the presence of a pair forward and reverse primers and a probe sequence which is complementary to an internal region of the target sequence, wherein one of the primers being labeled with a first label and the probe sequence being labeled with a second label such that amplification of the target sequence generates an amplicon labeled with both first and second labels; (b) applying an amount of the amplification product of step (a) to a lateral flow device/strip to flow laterally towards a distal end of the lateral flow device/strip, wherein the lateral flow device/strip sequentially comprising (i) a sample pad, (ii) a conjugate pad, (iii) a test region, and (iv) a control region, said conjugate pad having mobile reporter labeled with a first agent which specifically binds to the first label or the second label of the amplicon, said test region provided with a second agent which specifically binds to the second label or the first label of the amplicon to inhibit further lateral flow of the amplicon associated with the mobile reporter, and said control region being provided with a control agent; and (c) detecting any binding of the amplification product at the test region and the control region.

According to the present invention, the term "sample" may be a biological sample, for example any sample collected from an individual suspected of carrying CAEV. The sample may be any sample that contains the virus from an infected individual, and includes tissue and fluid samples, for example, blood, serum, plasma, peripheral blood cells including lymphocytes and mononuclear cells, sputum, mucous, urine, feces, throat swab samples, dermal lesion swab samples, cerebrospinal fluids, pus, and tissue including spleen, kidney and liver.

According to the present invention, a nucleic acid of the sample is extracted for further evaluation. Preferably, gDNA from the sample is first extracted, and then amplification of gag-segment (nt 618-803) DNA of CAEV, which is a relatively conserved region of the viral genome, by RPA reaction. By designing primer sequences that are specific to the gag-segment (nt 618-803) and avoiding the mutational hot spots in the virus sequence, the preferable forward primer is having a sequence of SEQ ID NO. 1 (TCA-GAGGGGAGCACTTGACAGAAGGAAATTGT) and the reverse primer is having a sequence of SEQ ID NO. 2 (CTAATGTGGCCTGCAAAGACATAAAGTCT). In addition, one of the primers is labeled with a first label. As the DNA target sequence is amplified during the amplification reaction, a probe with a second label, which is different to the first label, specifically hybridizes to an internal sequence within the amplicon, such that the amplicon is labeled with both first and second labels. More preferably, the probe sequence consisted of SEQ ID NO. 3 (GGGGAGCACTT-GACAGAAGGAAATTGTTTA) with 5'-second label and is connected a THF spacer to a downstream SEQ ID NO. 4 (GGTGCCTTAAAACAT) carrying a C3-spacer at its 3' end.

Preferably, the first and second labels are selected from haptens such as, for example, biotin, fluorescein derivatives (e.g. FITC or FAM), rhodamine derivatives (e.g. TAMRA), Cascade Blue, Lucifer yellow, 5-bromo-2-deoxyuridine (BrdU), dinitrophenol (DNP), digoxygenin (DIG), and short peptide label sequences (i.e. short peptides against which specific antibodies can be raised). More preferably, the first label is biotin and the second label is FAM, in which case, amplicons generated during the amplification step are labeled with both biotin and FAM.

Following the amplification, the amplification product is applied to a lateral flow device/strip. The lateral flow device/strip comprises a substrate which allows constituents of the buffered product to wick or flow laterally towards a distal end of the lateral flow device. Generally, the lateral flow device is in the form of a strip of the substrate. Preferably, the substrate is composed of nitrocellulose membrane, polyvinylidene fluoride (PVDF), nylon or a single porous material matrix. The lateral flow device comprises a sample pad and a conjugate pad at the proximal end, and at or adjacent to the distal end, with a test region (also known as test line) and a control region (also known as control line). The sample pad is for loading the amplification product, and when the amplification product flow laterally to the conjugate pad, mobile reporter labeled with a first agent in the conjugate pad will specifically binds to the first label or the second label of the amplicon.

The term "mobile reporter" refers to microparticles, which may be composed of a wide variety of substances, but are preferably composed of one or more substantially inert substances such as gold, silica, selenium, polystyrene, melamine resin, polymethacrylate, styrene/divinylbenzene copolymer, and polyvinyltoluene, labeled with a first agent. The microparticles are preferably non-porous. The microparticles may comprise a substance to allow for visualization of results at the test region and control region on the lateral flow device. Conveniently, such a substance will be a dye or other colored substance to allow for visualization with the unaided eye, however alternatively, the substance may be, for example, a label substance allowing visualization through the generation of a colored substance (e.g. an enzyme or other catalytic-label) or by fluorescence, luminescence or magnetic interactions (e.g. using a fluorimeter, luminometer or magnetic induction).

The first agent is selected from agents capable of specifically binding or reacting with the first label or the second label. As such, the first agent may be an antibody, antibody fragment (e.g. Fab, F(ab')2 and scfv fragments), receptor or other binding partner. The first agent itself may be conjugated to an enzyme or catalytic substance allowing visualization through the generation of a detectable product. Where the first label is biotin and the first agent is designed for the binding to the first label, then the first agent may be streptavidin or avidin, but more preferably, is an anti-biotin antibody.

The test region is provided with a second agent, which specifically binds to said second label or said first label. Binding of the second label or the first label of the second agent depends on the first agent and shall be different to the binding partner of the first agent. For example, if the first agent is designed for the binding to the first label, then the second agent shall bind to the second label. Preferably, the first label is biotin and the second label is FAM, and the first agent is designed for the binding to the second label, then first agent may be anti-FAM antibody, and the second agent may be streptavidin, avidin, or an anti-biotin antibody.

The test region provides a test result. That is, the test region binds and immobilizes amplicons (wherein each amplicon should be bound to a mobile reporter) and thereby provides a result showing the presence or absence in the sample of CAEV provirus intended to be detected. A "positive" test result (i.e. a test result indicating the presence of the CAEV provirus in the sample) is preferably indicated by the appearance of a visible color signal, as provided by the mobile reporter, at the test region. Where the mobile reporters are gold microparticles, the visible color signal will be a pinkish-red color.

The control region is a region on the lateral flow device/ strip separate from the test region. Preferably, the control region is located between the test region and the distal end of the lateral flow device/strip. The control region provides a positive control result. As described below, this positive control result can show that the mobile reporters have successfully flowed across the strip. Thus, in the simplest case, the control region is provided with a control agent specifically binds to the first agent, in which case the control region binds and immobilizes mobile reporters and thereby provides a result to indicate whether the mobile reporters have successfully flowed across the substrate of the strip.

[Kit of the Invention]

The invention also includes kits for carrying out the methods according to the invention.

The term "kit", as used in the present invention, refers to a combination of a set of reagents suitable for detecting a target DNA by a method according to the invention together with one or more types of elements or components (for example, other types of biochemical reagents, containers, packaging suitable for its commercial sale, substrates to which the reagents are bound, electronic hardware components, etc.).

The kit for detection of caprine arthritis-encephalitis virus (CAEV) in a sample, as a second aspect of the invention, comprising: a pair of forward and reverse primers targeting a gag-segment (nt 618-803) DNA of CAEV as a target sequence; a probe sequence which is complementary to an internal region of the target sequence; a reagent for conducting recombinase polymerase amplification (RPA) reaction; and a lateral flow device/strip; wherein one of the primers being labeled with a first label and the probe sequence being labeled with a second label such that amplification of the target sequence generates an amplicon labeled with both first and second labels; and the lateral flow device/strip sequentially comprising (i) a sample pad, (ii) a conjugate pad, (iii) a test region, and (iv) a control region, said conjugate pad having mobile reporter labeled with a first agent which specifically binds to the first label or the second label of the amplicon, said test region provided with a second agent which specifically binds to the second label or the first label and said control region being provided with a control agent.

The term "recombinase Polymerase Amplification (RPA)" is a process in which recombinase-mediated targeting of oligonucleotides to DNA targets is coupled to DNA synthesis by a polymerase. First, a recombinase agent is contacted with a first and a second nucleic acid primer to form a first and a second nucleoprotein primer. Second, the first and second nucleoprotein primers are contacted to a double stranded target sequence to form a first double stranded structure at a first portion of said first strand and form a double stranded structure at a second portion of said second strand so the 3' ends of said first nucleic acid primer and said second nucleic acid primer are oriented towards each other on a given template DNA molecule. Third, the 3' end of said first and second nucleoprotein primers are extended by DNA polymerases to generate first and second double stranded nucleic acids, and first and second displaced strands of nucleic acid. Finally, the second and third steps are repeated until a desired degree of amplification is reached. The necessary reagents for the RPA are described in US 2015/0240298A1, which is hereby incorporated by reference in its entirety.

Example

Hereinafter, the present disclosure will be specifically described with reference to examples and drawings. However, the present disclosure is not limited to the examples and the drawings.

[Materials and Methods]

Animal and Blood Samples

The blood samples were collected from 3 flocks of various breeds (94 heads of Alpine, 36 heads of Saanen, and 70 heads of Nubian) from different regions of Taiwan, one of which participated in the Taiwan National CAEV Control and Eradication Programme conducted by Taiwan's agriculture authority. The other two flocks, meanwhile, were previously identified as CAEV-positive flocks by serological tests. Both seronegative and seropositive goats, as identified by the presence or absence of anti-CAEV antibody by ELISA as described below, were sampled. Included among the seropositive animals were a number of goats exhibiting chronic arthromegaly ('big knee symptom'), which is a classic finding of CAEV infection. Both serum samples and EDTA-anticoagulated blood samples were collected from each of the 200 goats by jugular venipuncture. The animal protocols were approved by the Ethical Animal Usage Committee at Hsinchu Branch, Livestock Research Institute, Council of Agriculture, Executive Yuan.

Serological CAEV Diagnostic Tests

Sera were collected from clotted blood samples by centrifugation at 1,200×g for 20 min and then stored at −20° C. until needed. The presence or absence of antibodies to CAEV was analyzed using the commercially available ELISA kit, using CHEKIT maedi-visna virus (MVV)/CAEV whole virus ELISA from Bommeli Diagnostics (Liebefeld-Bern, Switzerland). The test was carried out following the instructions of the manufacturer.

Total DNA Template Preparation

Total DNA from EDTA-anticoagulated blood was extracted using a DNA isolation kit commercially available under the QIAamp® DNA Mini Kit (Qiagen, Courtaboeuf, France), following the manufacturer's instructions. The concentration and quality of DNA were determined using a NanoDrop 1000 Spectrophotometer (Thermo Fisher Scientific Inc., Waltham, Mass., USA) at 260 and 280 nm, and then adjusted to 50 ng/μL by DNase-free water. The quantified DNA was stored at −20° C. until RPA was performed. One microliter of the template was used in optimized RPA-LFD reaction. The DNA of goat pox virus and the RNA of bovine leukemia virus were extracted from cell cultures. The bovine leukemia virus RNA was amplified by reverse transcriptase PCR following the method of Rovnak and Casey (1999).

Recombinant Plasmid Construction

The CAEV gag gene sequences located between the nt positions 512 and 1858 of the CAEV proviral genome (GenBank accession number: M33677.1) were ordered and synthesized, and were then used to clone pUCIDT-AMP vector by Integrated DNA Technologies (IDT) (Coralville, Iowa, USA). According to the manufacturer's protocol for plasmid resuspension, the recombinant plasmid was centrifuged and re-suspended in 80 μL of IDTE (10 mM Tris, 0.1 mM EDTA) buffer (pH 7.5-8.0) to reach an approximate concentration of 50 ng/μL as a stock concentration and then stored in −20° C. until use. Two microliters of the template were used in each optimized RPA reaction.

Recombinase Polymerase Amplification Primer and Probe Design

Because the detailed mechanism of RPA is not yet fully understood, the amplification performance of a given oligonucleotide primer is based purely on its sequence. It is recommended that software-designed primers undergo an assay development process to screen a series of candidate primers and select a preferred primer pair. According to the appendix in the TwistAmp® DNA amplification reaction kit manual, a series of suitable (29-35 bp, GC content 30-70%) candidate RPA primers were designed using Primer3 to target the conserved regions in the CAEV gag gene (512-1858 nt, GenBank accession number: M33677.1) DNA sequences. Following the TwistAmp® DNA amplification reaction kit manual for primer screening, the normal forward primer P001 (SEQ ID NO. 1, 5'-TCAGAGGGGAGCACT-TGACAGAAGGAAATTGT-3', nt 618-649) and the reverse primer P002 with a 5'-biotin label (5'-biotin-CTAATGTG-GCCTGCAAAGACATAAAGTCT (SEQ ID NO. 2)-3', nt 775-803) for the detection of CAEV gag gene (nt 618-803, 186 bp) met our requirements satisfactorily using the TwistAmp® Basic DNA amplification kit (TwistDx, Cambridge, UK). Thereafter, two nfo DNA probes (LF probe 1 and LF probe 2) used for LFD assay were designed from the sequence between RPA primers. The probes consisted of an upstream stretch (30 nt) carrying a 5'-FAM antigenic label, and were connected via a THF spacer to an adjacent downstream oligonucleotide (15 nt) carrying a C3-spacer (polymerase extension blocking group) at its 3' end. The designed nfo probes were tested for their compatibility with the forward P001 and reverse P002 primers to amplify the CAEV gag gene (nt 512-1858) using a TwistAmp® nfo DNA amplification kit (TwistDx, UK) for lateral flow detection. The LF probe 1 (5'-FAM-GGGGAGCACTTGACA-GAAGGAAATTGTTTA (SEQ ID NO. 3)-THF-GGTGC-CTTAAAACAT (SEQ ID NO. 4)-C3-spacer-3') demonstrated the best target amplification (183 bp). The primers and the probes were synthesized by Integrated DNA Technologies (Coralville, Iowa, USA).

Recombinase Polymerase Amplification Conditions and Optimization

For primer screening, RPA was performed in a 50 μL volume using a TwistAmp® Basic DNA amplification kit (TwistDx, Cambridge, UK) with slight modifications to the manufacturer's protocol. The mixture of 1 ng of recombinant plasmid DNA, 0.42 μM of each RPA primer, 14 mM magnesium acetate, 1× of rehydration buffer, and DNase-free water was added to the dry enzyme pellet and thoroughly mixed. Magnesium acetate was pipetted into the tube lids, followed by centrifugation of the magnesium acetate into the tubes to initiate the RPA mechanism at 37° C. for 60 min. The reactions were visualized by 4% agarose gel electrophoresis (AGE). For probe screening, RPA was performed in a 50 μL volume using a TwistAmp® nfo DNA amplification kit (TwistDx, Cambridge, UK) for lateral flow detection. The P001 and P002 primers were adapted for the RPA assay by labeling the reverse P002 primer with a 5' biotin residue and testing both primers for compatibility with an internal RPA LF probe (LF probe 1 or LF probe 2) which was designed according to the TwistDx guidelines. Following the mixing of 0.42 μM of each RPA primer (P001 and P002) and 0.12 μM of an LF probe (LF probe 1 or LF probe 2) with 1× rehydration buffer and DNase-free water, the mixture was then added to the dry pellet of the Twist-Amp® nfo DNA amplification kit (TwistDx, Cambridge, UK) for lateral flow detection. The recombinant plasmid DNA (1 ng) was added, and 14 mM of magnesium acetate was pipetted into the tube lids, after which centrifugation was performed to initiate the RPA mechanism at 37° C. for 60 min. The reactions were visualized by 4% AGE.

For CAEV diagnosis of field samples, RPA was performed in a 50 μL volume using a TwistAmp® nfo DNA amplification kit (TwistDx, Cambridge, UK) for lateral flow detection. One μL of the field genomic DNA sample, 0.42 μM of each RPA primer (P001+P002 primers), 0.12 μM of LF probe 1, 14 mM magnesium acetate, 1× rehydration buffer, and DNase-free water were first mixed and added to the dry enzyme pellet. Magnesium acetate was pipetted into the tube lids. The lids were then closed, followed by centrifugation the magnesium acetate into the tubes to initiate the RPA mechanism. The tubes were then incubated at 37° C. for 30 min.

Lateral Flow Dipstick (LFD) Assay

The RPA amplicon was observed as a positive test line on the LFD strip (Milenia Biotec, Giessen, Germany). To detect the RPA amplicon by LFD, 2 μL of RPA product were added to a new tube containing 120 μL of the assay buffer (1× phosphate buffered saline with 0.1% of a detergent commercially available under TWEEN 20). The LFD strip was then dipped into the mixture for 5 min to visualize the test result. Namely, after dipping the LFD strip into the mixture, the constituents of the mixture were allowed to flow across the membrane, comprising a sample pad, a conjugate pad, a test region, and a control region. The conjugate pad has mobile reporters labeled with anti-FAM antibody so that the mobile reporters can bind with the amplicons doubly labeled with FAM and biotin. The test line comprising anti-biotin antibodies "trapped" doubly labeled amplicons. Doubly labeled amplicons were bound to mobile reporters, and thus, when trapped at the test line by anti-biotin antibodies, generated a pinkish-red line. On the other hand, the positive control line comprising secondary anti-FAM antibody trapped the mobile reporters that either were not bound to amplicons or were not captured by the anti-biotin antibody of the test line. The positive control line confirmed that the mobile reporters flowed across the membrane. Trapping of mobile reporters at the positive control line also generated a pinkish-red line. The entire LFD assay was performed at room temperature.

Molecular Specificity of RPA-LFD

The molecular specificity of the RPA-LFD assay using the RPA P001 and P002 primers and LF probe 1 was evaluated by cross-reaction tests using 100 ng of DNA or cDNA templates extracted from two other animal viruses, namely, goat pox virus and bovine leukemia virus, under the determined optimal conditions for CAEV detection. The virus specimens were provided by the Animal Health Research Institute, Council of Agriculture, Executive Yuan (Taiwan). The resulting products were analyzed with LFD and 4% AGE.

Evaluation of Molecular Sensitivity of RPA Using LFD and AGE

Five-fold serial dilutions of the total DNA extracted from a CAEV-infected goat at 50 ng, 10 ng, 2 ng, 400 pg, and 80 pg, and 10-fold serial dilutions of the plasmid DNA at $10^8$, $10^7$, $10^6$, $10^5$, $10^4$, $10^3$, $10^2$, and 10 copies were used as templates for RPA. The resulting DNA products were analyzed by LFD and AGE and were then compared.

Reliability and Positive Rate Comparison of RPA-LFD with Serological ELISA

The screening of samples from goats with unknown CAEV status was conducted using both the RPA-LFD assay and a serological ELISA kit as follows: (1) the RPA-LFD test was conducted according to procedures previously described for CAEV diagnosis of field samples using genomic DNA. (2) The serological ELISA test was conducted on serum samples using the CHEKIT MVV/CAEV whole virus ELISA from Bommeli Diagnostics (Liebefeld-Bern, Switzerland) following the instructions of the manufacturer. McNemar's test of agreement by the coefficient was also calculated, with 0 equal to no agreement beyond chance and 1.0 indicating perfect agreement between the RPA-LFD and ELISA tests.

[Results]

Determination of the RPA-LFD Conditions

Figure 1:
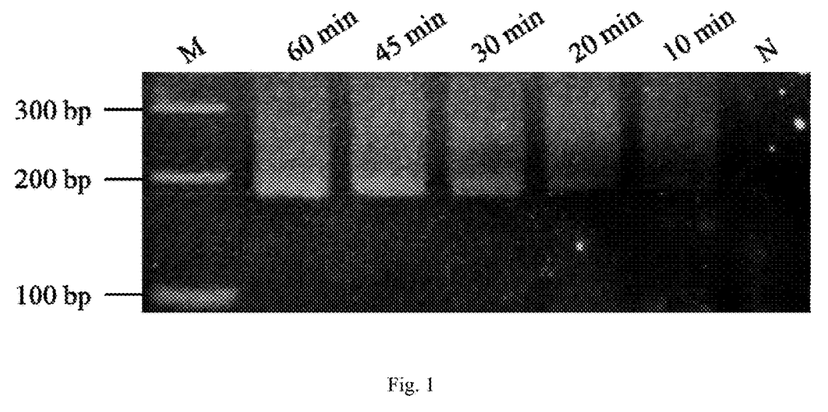
FIG. 1 shows optimisation of RPA reaction temperature using $10^2$ copies of CAEV gag gene recombinant plasmid DNA. Lanes M and N are molecular marker and negative control (DNase-free water), respectively.

The optimal temperature for RPA reactions was determined using $10^3$ copies and $10^2$ copies of plasmid DNA as templates, with the copies amplified at 37, 38, or 39° C., respectively. The amplification results, as determined by AGE, did not show significant differences for amplification at 37, 38, or 39° C. (data not shown). Thus, given the testing results and the manufacturer's instructions, 37° C. was selected as the assay temperature. For RPA reactions performed at 37° C. for 10, 20, 30, 45, and 60 min by using $10^2$ copies of plasmid DNA as templates, the quantities of amplification products at 30, 45, and 60 min were similar but higher than those at 10 and 20 min. In fact, the amplification products, as determined by AGE, were barely observable at 10 min and were only faintly observable at 20 min (FIG. 1). As such, for practical and efficient use in the field, an incubation time of 30 min was selected as optimal. The detection of RPA amplification products was also tested using LF strips. The amplification products were detectable after an incubation time as short as 10 min, and a clear positive test band was observed at 30 min (FIG. 1).

Molecular Specificity of RPA-LFD

Figure 2A:
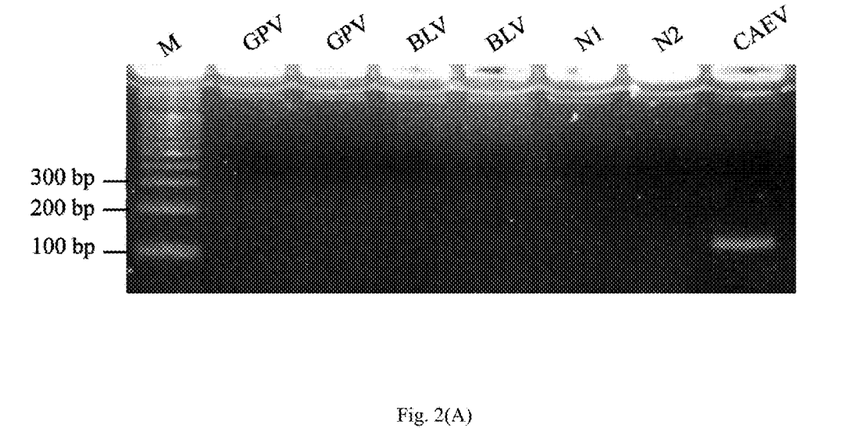
FIG. 2(A) shows results visualized by AGE.
Figure 2B:
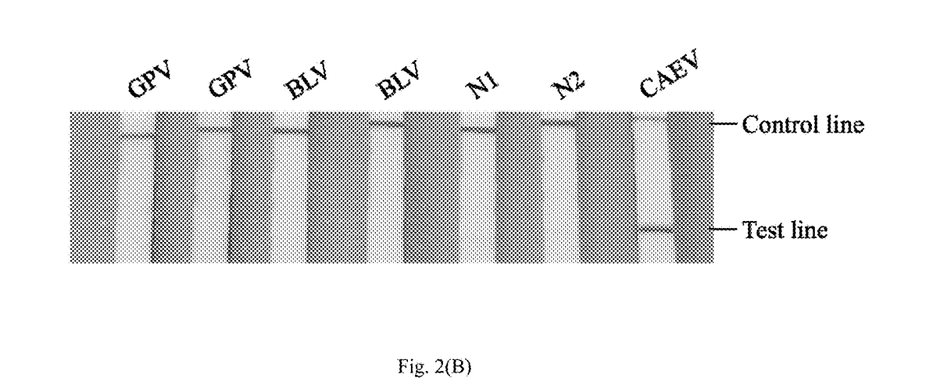
FIG. 2(B) shows results visualized by LFD. N1: total DNA extracted CAEV-negative goat. N2: negative control (DNase-free water).

For RPA P001 and P002 primers and LF probe 1 specificity testing at the optimal conditions, reactions were performed in conjunction with the DNA or cDNA from other vertebrate animal viruses. There were no cross-reactions when other vertebrate viruses such as goat pox virus and bovine leukemia virus were tested and detected by AGE (FIG. 2A) and LFD (FIG. 2B), indicating that the primers and the probe were specific for CAEV gag gene detection. Ladder-like patterns and primer/probe residuals were occasionally detected by AGE, however, under non-optimal conditions, such as non-optimal incubation temperature, non-optimal incubation time, and non-optimal template DNA quality and quantity. Therefore, the ability of the LFD assay to discriminate its target amplification product from non-related amplicons or primer/probe residuals was also evaluated. The LFD assay only gave positive results for its expected 186-bp target amplification product, that is, there were no false-positive results for no template control (NTC) with only primer/probe residuals, as determined by AGE, and showed only a red-purple color control line (FIG. 2B).

Comparative Molecular Sensitivity of the RPA-AGE and the RPA-LFD Assays

Figure 3A:
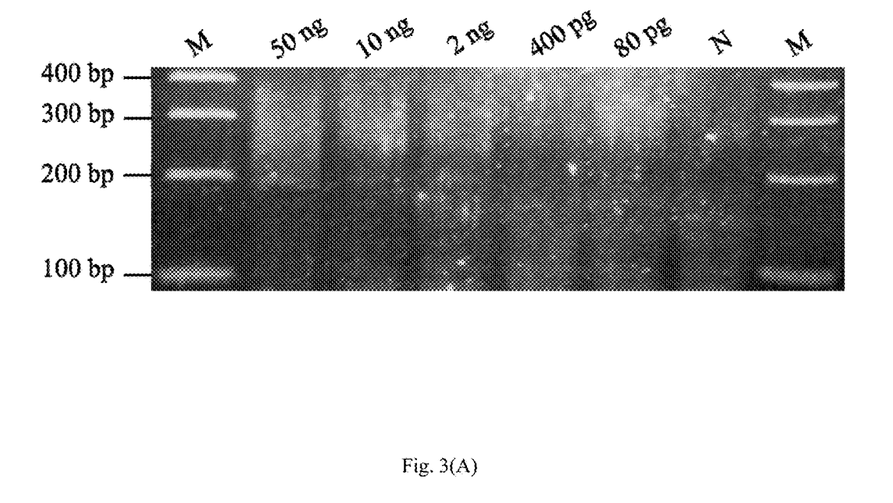
FIG. 3(A) shows results visualized by AGE.
Figure 3B:
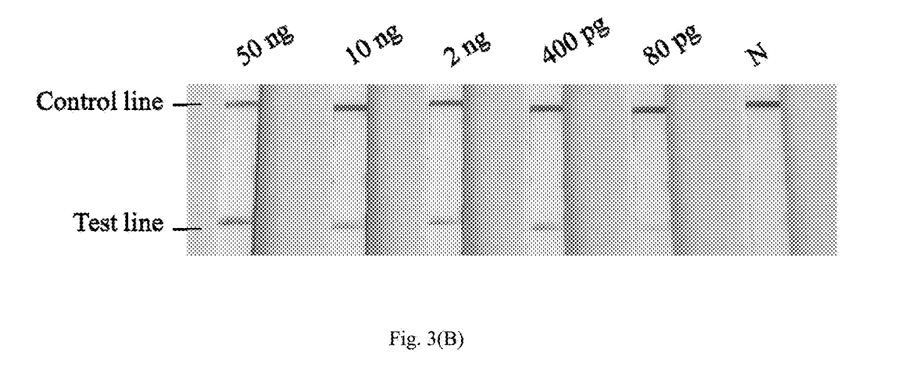
FIG. 3(B) shows results visualized by LFD for the same RPA amplicons. 50 ng, 10 pg, 2 ng, 400 pg and 80 pg: dilution series of total DNA prepared from CAEV-infected goat; N: no-template control (DNase-free water).
Figure 4A:
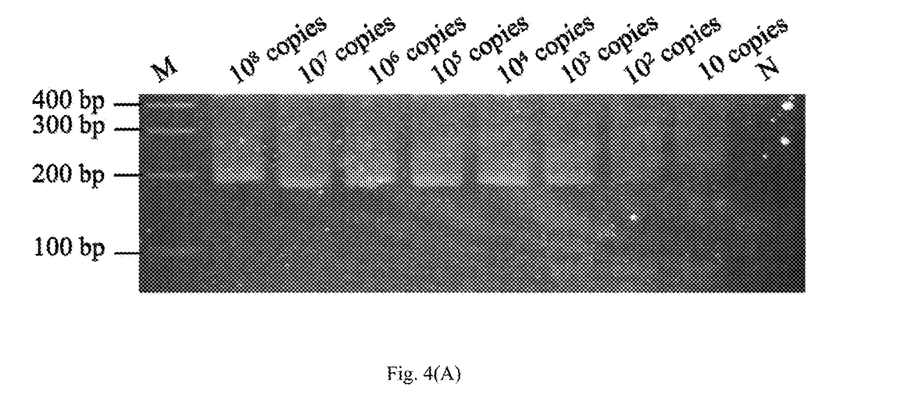
FIG. 4(A) shows results visualized by LFD.

When testing the sensitivity of the RPA-LFD assay using 5-fold serial dilutions of the total DNA extract, a detection limit of 80 pg caprine total DNA was found (FIG. 3B). This was 625 times greater than the detection limit of the RPA-AGE assay, which was 50 ng (FIG. 3A). When the recombinant plasmids were used as templates, the RPA-LFD assay showed a detection limit with a positive signal at 10 copies (FIG. 4B), but the RPA-AGE only gave a faint band at 100 copies (FIG. 4A). These results indicated that using LFD for the detection of RPA product had a higher sensitivity than the use of AGE to detect the RPA product, which the yielding more strong positive signals by the LFD even when the detection by AGE was not clear.

Reliability and Positive Rate Comparison of the RPA-LFD Assay with Serological ELISA To evaluate the statistical sensitivity and specificity of the RPA-LFD assay, it was applied in parallel with the traditional ELISA assay using field samples. A comparison of the results of the ELISA and RPA-LFD assays is shown in Table 1. Of the 200 goats sampled and tested with ELISA and RPA-LFD, 157 (78.5%) heads were positive to both assays. Out of the 200 goats, 43 (21.5%) and 36 (18.0%) heads were negative to ELISA and RPA-LFD, respectively, with seven out of the 43 (3.5%) seronegative goats being RPA-LFD positive. The RPA-LFD assay thus had significantly higher CAEV-positive rate (82.0%) than did the ELISA assay (78.5%) (P<0.05). The coefficient was 0.89, indicating a very strong agreement between the two assays.

TABLE 1

Diagnostic performance of the RPA-LFD CAEV assay.

| PRA-LFD | CAEV status diagnosed by reference ELISA assay | |
|---|---|---|
| | Positive | Negative |
| Positive | 157 | 7 |
| Negative | 0 | 36 |

The higher sensitivity and specificity demonstrated by the LFD method were attributed to the use of gold-labeled anti-FAM antibodies to capture FAM-labeled RPA amplicon specifically, which had the ability to discriminate the target amplicon from non-related amplicons under non-optimal amplification conditions. Even in cases in which the quantity of the amplification products was so low as to almost be invisible on AGE, the LFD method could still provide a visible band on the strip (FIG. 3). It is obvious that the LFD assay possesses high selectivity against occasionally mismatched DNA target sequences by confirming the identity of RPA amplicon, while it also provides better sensitivity than the AGE method. Without the hybridization step of amplicons and probes, the detection of RPA amplicon by LFD is simple and can be determined within 5-15 min at room temperature.

Figure 4B:
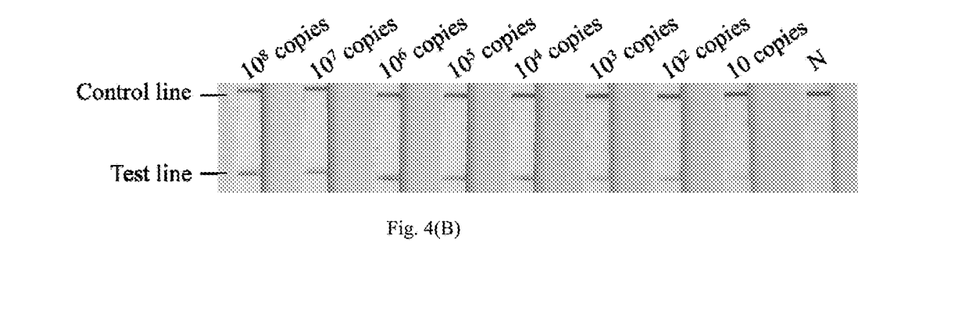
FIG. 4(B) shows results visualized by AGE for the same RPA products. Lanes M and N: molecular marker and negative control (DNase-free water), respectively.

In the present invention, an RPA method has been successfully developed to amplify the gag gene region of CAEV, and the amplicon can be easily detected by a semi-quantitative colorimetric change on the LF strip (FIG. 4B). Amplification was detectable after only 30 min of incubation at 37° C.; thus, performing incubation through the use of a heat block, water bath, battery-powered device, or even human body temperature in endemic areas would suffice, removing the need for external power supplies and infrastructure. The present invention also shows that the RPA-LFD assay provides a significantly higher CAEV-positive rate than does an ELISA assay (P<0.05), a result which may be due to the fact that the RPA can theoretically detect even a single template DNA copy. In clinical evaluations, the results have also showed that the RPA-LFD assay is more sensitive than regular ELISA assays. These results also indicate that CAEV could be detected by the RPA-LFD assay in the absence of detectable antibody.

Therefore, the invention provides a sensitive and specific RPA-LFD field-diagnostic method for detecting CAEV proviral DNA in a simple, rapid, and cost-effective manner. The combination of RPA amplification and LFD detection results in a total assay time of approximately 35 min, which is only a quarter of the assay time of RPA-AGE and is about 6 times faster than the ELISA method currently used for the detection of CAEV. The high sensitivity and specificity, the short detection time, and the amplicon confirmation by lateral flow hybridization are the key advantages of this method. This procedure requires no other equipment besides a simple heating block, making the diagnosis of CAEV infections possible in less-well-equipped laboratories or even in the field.

While example embodiments have been disclosed herein, it should be understood that other variations may be possible. Such variations are not to be regarded as a departure from the spirit and scope of example embodiments of the present application, and all such modifications as would be obvious to one skilled in the art are intended to be included within the scope of the following claims.

What is claimed is:

1. A method for detection of caprine arthritis-encephalitis virus (CAEV) infection, comprising the steps of:
   (a) amplifying gag-segment (nt 618-803) DNA of CAEV as a target sequence in the sample by recombinase polymerase amplification (RPA) in the presence of a pair forward and reverse primers and a probe sequence which is complementary to an internal region of the target sequence, wherein one of the primers being labeled with a first label and the probe sequence being labeled with a second label such that amplification of the target sequence generates an amplicon labeled with both first and second labels;
   (b) applying an amount of the amplification product of step (a) to a lateral flow device/strip to flow laterally towards a distal end of the lateral flow device/strip, wherein the lateral flow device/strip sequentially comprising (i) a sample pad, (ii) a conjugate pad, (iii) a test region, and (iv) a control region, said conjugate pad having mobile reporter labeled with a first agent which specifically binds to the first label or the second label of the amplicon, said test region provided with a second agent which specifically binds to the second label or the first label of the amplicon to inhibit further lateral flow of the amplicon associated with the mobile reporter, and said control region being provided with a control agent; and
   (c) detecting any binding of the amplification product at the test region and the control region.

2. The method of claim 1, wherein the first and second labels are selected from biotin, fluorescein derivatives, rhodamine derivatives, Cascade Blue, Lucifer yellow, 5-bromo-2-deoxyuridine (BrdU), dinitrophenol (DNP), digoxygenin (DIG), and short peptide label sequences.

3. The method of claim 1, wherein the forward primer comprises a sequence of SEQ ID NO: 1 and the reverse primer comprises a sequence of SEQ ID NO: 2.

4. The method of claim 3, wherein the reverse primer comprises a 5'-biotin label.

5. The method of claim 3, wherein the probe sequence consists of SEQ ID NO: 3 with 5'-FAM antigenic label and a downstream SEQ ID NO: 4 carrying a C3-spacer at its 3' end, wherein SEQ ID NO: 3 and SEQ ID NO: 4 is connected by a THF spacer.

6. The method of claim 4, wherein the mobile reporter is a microparticle of gold, silica, selenium, polystyrene, melamine resin, polymethacrylate, styrene/divinylbenzene copolymer or polyvinyltoluene.

7. A kit for detection of caprine arthritis-encephalitis virus (CAEV) in a sample, comprising:
   a pair of forward and reverse primers targeting a gag-segment (nt 618-803) DNA of CAEV as a target sequence;
   a probe sequence which is complementary to an internal region of the target sequence;
   a reagent for conducting recombinase polymerase amplification (RPA) reaction; and
   a lateral flow device/strip;
   wherein one of the primers being labeled with a first label and the probe sequence being labeled with a second label such that amplification of the target sequence generates an amplicon labeled with both first and second labels; and the lateral flow device/strip sequentially comprising (i) a sample pad, (ii) a conjugate pad, (iii) a test region, and (iv) a control region, said conjugate pad having mobile reporter labeled with a first agent which specifically binds to the first label or the second label of the amplicon, said test region provided with a second agent which specifically binds to the second label or the first label and said control region being provided with a control agent.

8. The kit of claim 7, which further comprises a reagent for extracting nucleic acid from the sample.

9. The kit of claim 8, wherein the forward primer comprises sequence of SEQ ID NO: 1 and the reverse primer comprises a sequence of SEQ ID NO: 2.

10. The kit of claim 9, wherein the reverse primer comprises a 5'-biotin label.

11. The kit of claim 10, wherein the probe sequence consists of SEQ ID NO: 3 with 5'-FAM antigenic label and a downstream SEQ ID NO: 4 carrying a C3-spacer at its 3' end, wherein SEQ ID NO: 3 and SEQ ID NO: 4 is connected by a THF spacer.

12. The kit of claim 11, wherein the mobile reporter is a microparticle labeled with an anti-FAM antibody.

13. The kit of claim 12, wherein the control agent is a secondary antibody of the anti-FAM antibody.

* * * * *